United States Patent
Ohno et al.

(10) Patent No.: US 7,179,653 B2
(45) Date of Patent: Feb. 20, 2007

(54) MEASURING METHOD FOR CONCENTRATION OF HALOGEN AND FLUORINE COMPOUND, MEASURING EQUIPMENT THEREOF AND MANUFACTURING METHOD OF HALOGEN COMPOUND

(75) Inventors: Hiromoto Ohno, Kawasaki (JP); Toshio Ohi, Kawasaki (JP); Kazunari Kaga, Kawasaki (JP); Ryuichi Tachi, Kawasaki (JP); Itsuaki Matsuda, Yokohama (JP)

(73) Assignee: Showa Denko K.K., Tokyo (JP)

( * ) Notice: Subject to any disclaimer, the term of this patent is extended or adjusted under 35 U.S.C. 154(b) by 1022 days.

(21) Appl. No.: 09/822,211

(22) Filed: Apr. 2, 2001

(65) Prior Publication Data

US 2002/0051132 A1    May 2, 2002

Related U.S. Application Data

(60) Provisional application No. 60/216,517, filed on Jul. 6, 2000, provisional application No. 60/216,519, filed on Jul. 6, 2000.

(30) Foreign Application Priority Data

| Mar. 31, 2000 | (JP) | ............................. 2000-098453 |
| Apr. 28, 2000 | (JP) | ............................. 2000-129417 |
| Mar. 16, 2001 | (JP) | ............................. 2001-075570 |

(51) Int. Cl.
  *G01N 33/00*   (2006.01)

(52) U.S. Cl. ....................... 436/124; 436/164

(58) Field of Classification Search ................ 436/124, 436/164
  See application file for complete search history.

(56) References Cited

U.S. PATENT DOCUMENTS 2,925,327 A * 2/1960 Katz et al. .................... 422/83

(Continued)

FOREIGN PATENT DOCUMENTS

EP           031519            7/1981

(Continued)

OTHER PUBLICATIONS

J. Amer. Chem. Soc., 77, 3007, 1955, Edward A. Tyczkowski and Lucius A. Bigelow, "The Action of Elementary Fluorine upon Organic Compounds. XIX. A New Jet Fluorination Reactor."

(Continued)

*Primary Examiner*—Monique T. Cole
(74) *Attorney, Agent, or Firm*—Sughrue Mion, PLLC (57) ABSTRACT

The present invention provided a method for measuring a halogen gas and/or a hydrofluorocarbon for the purpose of controlling the concentration of the halogen gas and/or the hydrofluorocarbon, in a plant producing a halogen compound or a perfluorocarbon, at a predetermined concentration level quickly, easily, and precisely for the control. The present invention provides also a measurement apparatus for the above measurement which has a compact structure, and in which the parts are exchangeable quickly and readily. The present invention provides further a process for producing a halogen compound or a perfluorocarbon employing the measurement method and the measurement apparatus.

In particular, the present invention intends to provide a method for measuring safely and quickly a hydrofluorocarbon concentration in a mixed gas stream in a process of producing a perfluorocarbon by direct fluorination reaction of a hydrofluorocarbon and $F_2$.

10 Claims, 5 Drawing Sheets

U.S. PATENT DOCUMENTS

| | | | |
|---|---|---|---|
| 3,413,199 A * | 11/1968 | Morrow, Jr. | 205/780 |
| 4,049,382 A * | 9/1977 | Ross et al. | 205/780 |
| 4,937,398 A | 6/1990 | Tung et al. | |
| 4,938,926 A * | 7/1990 | Reiss | 422/58 |
| 5,149,659 A * | 9/1992 | Hakuta et al. | 436/55 |
| 5,300,442 A * | 4/1994 | Frant | 205/778.5 |
| 5,406,008 A | 4/1995 | Sievert | |
| 5,710,351 A | 1/1998 | Ohno et al. | |
| 5,714,648 A | 2/1998 | Ohno et al. | |
| 5,821,537 A * | 10/1998 | Ishihara et al. | 250/339.13 |
| 5,869,342 A * | 2/1999 | Stannard et al. | 436/55 |
| 6,040,915 A * | 3/2000 | Wu et al. | 356/435 |
| 6,274,879 B1 * | 8/2001 | Best-Timmann | 250/573 |
| 6,706,089 B1 * | 3/2004 | Landau | 95/48 |
| 6,720,464 B2 * | 4/2004 | Ohno et al. | 570/169 |

FOREIGN PATENT DOCUMENTS

| | | |
|---|---|---|
| EP | 032210 | 7/1981 |
| JP | 63-027736 | 2/1988 |
| JP | 63-247655 | 10/1988 |
| JP | 63247655 * | 10/1988 |
| JP | 02-207052 | 8/1990 |
| JP | 09-241186 | 9/1997 |
| JP | 09-241187 | 9/1997 |
| JP | 2000-022255 | 1/2000 |

OTHER PUBLICATIONS

J. Amer. Chem. Soc., 82, 5827, 1960, Abe F. Maxwell, Fredric E. Detoro and Lucius A. Bigelow, "The Action of Elementary Fluorine upon Organic Compounds. XXIII. The Jet Fluorination of Certain Aliphatic Hydrocarbons as Oriented and Controlled by Operating Conditions."

* cited by examiner

MEASURING METHOD FOR CONCENTRATION OF HALOGEN AND FLUORINE COMPOUND, MEASURING EQUIPMENT THEREOF AND MANUFACTURING METHOD OF HALOGEN COMPOUND

CROSS-REFERENCE TO RELATED APPLICATION

This application is an application filed under 35 U.S.C. §111(a) claiming benefit pursuant to 35 U.S.C §119(e)(1) of the filing date of Provisional Applications 60/1216,519 and 60/216,517 both filed on Jul. 6, 2000 pursuant to 35 U.S.C. §111(b).

FIELD OF THE INVENTION

The present invention relates to a method for measuring a concentration of a halogen and/or a fluorine compound in a gas, a measurement apparatus therefor, and a process for producing a halogen compound employing the measurement apparatus.

BACKGROUND OF THE INVENTION

Iodometry is known as a method for determining the concentration of a halogen gas. The iodometry is a widely employed titration method for determining a halogen indirectly by oxidizing the iodine ion, a weak reducing agent, with a halogen, a strong oxidizing agent, to iodine, and titrating the liberated iodine. The iodometry is applicable to quantitative determination of a halogen such as chlorine and fluorine, and oxygen acid salts thereof.

A measurement apparatus employing the iodometry is disclosed in Japanese Patent Application Laid-Open No. 63-247655. This apparatus determines fluorine by converting fluorine to iodine gas which has a light absorption coefficient higher than the fluorine gas and has the maximum light absorption coefficient in the visible light region. This fluorine-detecting apparatus is provided with a converter for converting fluorine gas to iodine gas, and a detector for determining fluorine by optically detecting the iodine gas formed by conversion with the converter. Specifically, fluorine is converted to iodine gas in the fluorine/iodine converter. For example, the converter is constituted of a first reaction column packed with potassium chloride particles and a second reaction column packed with potassium iodide particles; fluorine gas is converted to chlorine in the first column packed with potassium chloride, and the chlorine is introduced into the second reaction column to react with the potassium iodide to liberate iodine ($I_2$).

An indirect method for determining a halogen concentration is known in which a halogen gas is converted into another gas and measured the concentration of the gas and the concentration of the halogen gas is indirectly determined. For example, Japanese Patent Application Laid-Open No. 63-27736 discloses a gas concentration measurement apparatus which is constituted of a packing material for converting fluorine gas to another gas capable of absorbing infrared ray, a gas cell having an optical window transparent to the infrared ray on each of the side walls, a light source projecting infrared ray through the optical window, a detector for receiving the transmitted light from the gas cell, and a concentration meter for calculating the concentration of the converted gas from the output of the detector. The packing material is, for example, sulfur prepared by pulverizing crystalline sulfur. This packed sulfur material converts the fluorine gas to sulfur hexafluoride capable of absorbing infrared ray.

Any of the above methods measures the halogen concentration indirectly by converting the halogen gas once to another compound and measuring the concentration of the resulting converted compound. Therefore, the measurement results are obtained with a delay, which is not suitable for controlling the halogen gas concentration in a process at a prescribed level.

Usually, in a process for producing a halogen compound, the halogen gas is used desirably in excess of the substrate to conduct the halogenation effectively by keeping the halogen gas to be present in the reaction gas throughout the reaction. However, use of a large excess of the halogen gas is not economical owing to the necessity of a recovery system therefor. The amount of the halogen gas is decided depending on the kind of the substrate, the reaction temperature, and presence or absence of a catalyst. In a continuous production process, it is important to keep the halogen concentration within a suitable range. For measuring continuously the halogen concentration for example, the fluorine gas concentration, at a production site in the plant, methods are known as below:

(1) use of a fluorine detector employing an electrochemical cell;
(2) a method of introducing the objective gas into a potassium iodide solution and titrating automatically the iodine formed by reaction with fluorine gas by sodium thiosulfate; and so forth.

The above method (1), although it is useful for measuring temporarily fluorine in a gas containing the fluorine at a low concentration, is not useful for the object of the present invention, since the cell will deteriorate in a short time in continuous analysis of a fluorine containing gas. The above method (2), which automates a general method of fluorine determination in a gas, has disadvantages of low response speed owing to relatively long time required for the analysis, complicate maintenance, a relatively large space for the apparatus installation, and so forth.

Japanese Patent Application Laid-Open No. 2000-22255 describes a method of continuous analysis of fluorine in a gas. This method is applicable to direct measurement of a fluorine gas concentration in a gas mixture to control stably the fluorine gas concentration in real time. This method is employed for measurement of a concentration of a fluorine-containing gas mixture, for example, a gas used in an excimer laser apparatus by detecting the fluorine gas concentration from change in UV absorption of the fluorine gas. In this patent specification, a mixed gas is employed which contains Kr gas, or Ne gas in addition to the fluorine gas at a fluorine gas concentration of 1.0%, or 9.0%, for example.

However, this method involves problems in measurement of a fluorine gas concentration in a fluorine compound production process. Specifically, in a process for fluorinating a hydrocarbon or a hydrofluorocarbon by fluorine gas to produce a perfluorocarbon, the reaction generates a great amount of reaction heat: a larger amount of heat with increase of the amount of the fluorine, in proportion to the moles of the fluorine reacted. The great heat generation is liable to cause scission of the C—C bond, explosion, or the like, and lowering of the product yield, which are problems in industrial production and operation. To suppress the violent generation of the reaction heat, the fluorine gas is diluted with an inert gas (nitrogen, helium, etc.). Further, the method has another problem. That is, the gas after the reaction contains the perfluorocarbon as the reaction product and hydrogen fluoride equimolar to the substituted hydrogen, which lowers significantly the fluorine concentration. The continuous measurement of light absorbance of this fluorine in the gas mixture is difficult owing to the low fluorine concentration and influence of the other mixed gas depending on the maximum absorption wavelengths ($\lambda_{max}$/nm) and the molar absorption coefficients (unit: $mol^{-1}dm^3cm^{-1}$) of the component gases.

On the other hand, perfluorocarbons such as tetrafluoromethane and hexafluoroethane are used as an etching gas or a cleaning gas in semiconductor device production processes. Regarding the production process for such a fluorocarbon, various methods are known, for example, as shown below:

(1) reaction of ethane with $F_2$ in a jet reactor to form tetrafluoromethane (hereinafter occasionally referred to as "FC-14" or "$CF_4$"), or hexafluoroethane (hereinafter occasionally referred to as "FC-116" or "$CF_3CF_3$") with nitrogen gas used as the diluent gas (J.Am.Chem.Soc., 77, 3007 (1955); J.Am.Chem.Soc., 82, 5827 (1960));

(2) fluorination of C—H with $F_2$ in a reactor having a porous alumina tube (EP31519);

(3) fluorination of a linear hydrocarbon with $F_2$ in the presence of a diluent gas in a reactor having a porous metal tube (double tube structure): $SF_6$, $CF_4$, $C_2F_6$ or $C_3F_8$ being used as the diluent gas (EP32210); and (4) reaction of a saturated or unsaturated hydrocarbon, or a partially fluorinated hydrocarbon with $F_2$ to produce a hydrofluorocarbon (U.S. Pat. No. 5,406,008), or reaction of an alkene with carbon containing $F_2$ by adsorption to produce a fluorinated alkene (Japanese Patent Application Laid-Open No. 2-207052).

However, these methods are not necessarily satisfactory for the purpose of safe and efficient production of a perfluorocarbon.

Other methods are disclosed as below:

(5) reaction of a hydrofluorocarbon with $F_2$ in a gas phase in the presence of a diluent gas at an elevated temperature (Japanese Patent Application Laid-Open Nos. 9-241186, and 9-241187). In these method, a perfluorocarbon is produced safely and efficiently by reaction with $F_2$ at an elevated temperature by keeping the hydrofluorocarbon concentration at the reactor inlet to be not higher than 8 mole % by use of a diluent gas.

For conducting the direct fluorination reaction safely, the hydrofluorocarbon concentration at the reactor inlet should be analyzed and controlled precisely and quickly. Conventionally, in quantitative determination of a hydrofluorocarbon in a gas stream at the reactor inlet, a part of the mixed gas is sampled, and washed with a potassium iodide solution, and then (1) the acid gas components such as HF and $F_2$ are determined quantitatively by iodometric titration or neutralization titration of a part of the washing solution, and (2) the washed gas is analyzed by gas chromatography to determine the hydrofluorocarbon, the perfluorocarbon, and other minor gas components.

However, this analysis method involves a certain time lag between the start of the sampling of the gas mixture and the completion of the analysis, and is not suitable for the reaction process control. Furthermore, the gas sampling, the iodometric titration, and the neutralization titration have to be conducted manually, which compels the worker to handle the sample materials containing dangerous corrosive HF and $F_2$ gases.

OBJECT OF THE INVENTION

The present invention has been made on the aforementioned background. The present invention intends to provide a method for measuring a halogen gas and/or a hydrofluorocarbon for the purpose of controlling quickly, easily, and precisely the concentration of the halogen gas and/or the hydrofluorocarbon, in a plant producing a halogen compound or a perfluorocarbon, at a predetermined concentration level. The present invention intends also to provide a measurement apparatus for the above measurement which has a compact structure, and in which the parts are exchangeable quickly and readily. The present invention intends further to provide a process for producing a halogen compound or a perfluorocarbon employing the measurement method and the measurement apparatus.

In particular, the present invention intends to provide a method for measuring safely and quickly a hydrofluorocarbon concentration in a gas mixture stream in the process of producing a perfluorocarbon by direct fluorination reaction of a hydrofluorocarbon and $F_2$.

SUMMARY OF THE INVENTION

The inventors of the present invention, after comprehensive investigation, found that the halogen gas concentration can be measured continuously by projecting visible light to a solution containing iodine formed continuously and measuring the light transmittance. The inventors of the present invention found further that, in a process for producing perfluorocarbon by reaction of a hydrofluorocarbon with gaseous fluorine, the hydrofluorocarbon in the gas mixture stream can be determined quantitatively by introducing a part of the gas mixture stream into a measurement cell and measuring it using an infrared spectrometry. Furthermore, the inventors of the present invention found a measurement apparatus for the measurement, and a process for producing a halogen compound or a perfluorocarbon compound. Thus, the present invention has been completed. The present invention provides a method for measuring a halogen concentration and/or a hydrofluorocarbon concentration, a measurement apparatus therefor, and a process employing the method and the apparatus for producing a halogen compound and/or a perfluorocarbon compound as shown in (1) to (38) below:

(1) A method for measuring a halogen concentration comprising introducing a gas containing a halogen gas into a metal iodide-containing solution to liberate iodine, and determining quantitatively the liberated iodine by measuring a visible light transmittance of the solution at a specific wavelength.

(2) The method for measuring a halogen concentration as described in (1) above, wherein the metal iodide-containing solution contains starch.

(3) The method for measuring a halogen concentration as described in (1) above, wherein the specific wavelength ranges from 460 nm to 520 nm.

(4) The method for measuring a halogen concentration as described in (2) above, wherein the specific wavelength ranges from 580 nm to 780 nm.

(5) The method for measuring a halogen concentration as described in (3) or (4) above, wherein the visible light is a laser beam.

(6) The method for measuring a halogen concentration as described in (1) or (2) above, wherein the halogen gas is chlorine gas or fluorine gas.

(7) A method for continuously measuring a halogen concentration, comprising introducing continuously a gas containing a halogen gas into a continuously flowing metal iodide-containing solution to liberate iodine, and determining quantitatively the liberated iodine by measuring a visible light transmittance of the solution at a specific wavelength.

(8) The method for continuously measuring a halogen concentration as described in (7) above, wherein the metal iodide-containing solution contains starch.

(9) The method for continuously measuring a halogen concentration as described in (7) above, wherein the specific wavelength ranges from 460 nm to 520 nm.

(10) The method for continuously measuring a halogen concentration as described in (8) above, wherein the specific wavelength ranges from 580 nm to 780 nm.

(11) The method for continuously measuring a halogen concentration as described in (9) or (10) above, wherein the visible light is a laser beam.

(12) The method for continuously measuring a halogen concentration as described in (7) or (8) above, wherein the halogen gas is chlorine gas or fluorine gas.

(13) A method for measuring a hydrofluorocarbon concentration, comprising measuring a concentration of at least one kind of hydrofluorocarbon in a gas mixture by infrared spectrometry.

(14) The method for measuring a hydrofluorocarbon concentration as described in (13) above, wherein the hydrofluorocarbon concentration is not higher than 8 mole %.

(15) The method for measuring a hydrofluorocarbon concentration as described in (13) or (14) above, wherein the gas mixture contains a perfluorocarbon, and hydrogen fluoride and/or fluorine, and the concentrations of the perfluorocarbon and/or the hydrogen fluoride are measured simultaneously by infrared spectroscopy.

(16) The method for measuring a hydrofluorocarbon concentration as described in (15) above, wherein the gas mixture is rich in the perfluorocarbon and/or the hydrogen fluoride.

(17) The method for measuring a hydrofluorocarbon concentration as described in (13) above, wherein condensation of a gas on a surface of a measurement cell is prevented by heating the measurement cell.

(18) The method for measuring a hydrofluorocarbon concentration as described in (17) above, wherein hydrogen fluoride gas is removed after the gas concentration measurement by introducing a purge gas into the heated measurement cell.

(19) The method for measuring a hydrofluorocarbon concentration as described in (13) above, wherein the hydrofluorocarbon is represented by General Formula (1):

$$C_xH_yF_z \quad (1)$$

where x, y, and z are respectively an integer satisfying the relations: $1 \leq x \leq 3$, $1 \leq y \leq 4$, $1 \leq z \leq 7$, and $2x+2=y+z$.

(20) The method for measuring a hydrofluorocarbon concentration as described in (13) above, wherein the hydrofluorocarbon is trifluoromethane, 1,1,1,2-tetrafluoroethane and/or pentafluoroethane, and the concentration thereof is measured respectively at a wavenumber ranging from 2900 $cm^{-1}$ to 3100 $cm^{-1}$ as the measurement wavenumber.

(21) The method for measuring a hydrofluorocarbon concentration as described in (15) above, wherein the perfluorocarbon is tetrafluoromethane and/or hexafluoroethane, and the concentration thereof is measured respectively at a wavenumber ranging from 1000 $cm^{-1}$ to 2700 $cm^{-1}$ as the measurement wavenumber.

(22) The method for measuring a hydrofluorocarbon concentration as described in (15) above, wherein the concentration of hydrogen fluoride in the gas mixture is measured at a wavenumber ranging from 3600 $cm^{-1}$ to 4300 $cm^{-1}$ as the measurement wavenumber.

(23) A measurement apparatus for continuously measuring a halogen concentration for use in the continuous measurement of a halogen concentration as described in (7) above, comprising a reaction section for liberating iodine; a liquid feed pump for introducing a metal iodide-containing solution into the reaction section; an introduction tube for sampling a part of a reaction gas containing a halogen gas from a halogen compound production line; a gas flow rate controller connected to the introduction tube and serving to introduce continuously the halogen-containing gas into the reaction section; a gas-liquid separation section for separating an undissolved gas; a measurement section equipped with a visible light source for emitting visible light for measurement of iodine liberated in the reaction section, and a detector for measuring a transmittance of the visible light; and a data processing section.

(24) A measurement apparatus for continuously measuring a halogen concentration for use in the continuous measurement of a halogen concentration as described in (8) above, comprising a reaction section for liberating iodine; a liquid feed pump for introducing a solution containing a metal iodide and starch into the reaction section; an introduction tube for sampling a part of a reaction gas containing a halogen gas from a halogen compound production line; a gas flow rate controller connected to the introduction tube and serving to introduce continuously the halogen-containing gas into the reaction section; a gas-liquid separation section for separating an undissolved gas; a measurement section equipped with a visible light source for emitting visible light for measurement of iodine liberated in the reaction section, and a detector for measuring a transmittance of the visible light; and a data processing section.

(25) The measurement apparatus for continuously measuring a halogen concentration as described in (23) or (24) above, wherein the visible light source is a laser device.

(26) The measurement apparatus for continuously measuring a halogen concentration as described in (25) above, wherein the laser device is a semiconductor laser device.

(27) An apparatus for measuring a hydorfluorocarbon concentration for the method for measuring a hydrofluorocarbon concentration in a gas mixture as described in (13) above, comprising a measurement cell equipped with a heating means; an introduction tube for sampling a part of a reaction gas from a perfluorocarbon production line; automatic switching valve connected with the introduction tube and a purge gas introduction tube for controlling and switching quantity of introduction of the reaction gas and a purge gas into the measurement cells; an infrared spectrometer; and a data processing device having a calibration curve installed therein.

(28) The apparatus for measuring a hydorfluorocarbon concentration as described in (27) above, wherein the measurement cell has an optical window made from calcium fluoride for transmitting infrared ray (29) A process for producing a halogen compound by reaction of an organic compound with a halogen gas in a gas phase, wherein the halogen concentration is adjusted by the method for continuously measuring a halogen concentration as described in (7) above.

(30) The process for producing a halogen compound as described in (29) above, wherein the halogen gas is chlorine gas or fluorine gas.

(31) The process for producing a halogen compound as described in (29) or (30) above, wherein the organic compound is at least one hydrofluorocarbon represented by General Formula (2):

$$C_aH_bF_c \quad (2)$$

where a, b, and c are respectively an integer satisfying the relations: $1 \leq a \leq 3$, $1 \leq b \leq 4$, $1 \leq c \leq 7$; and b+c=4 for a=1, b+c=6 for a=2, and b+c=8 for a=33;

and/or at least one fluoroolefin represented by General Formula (3):

$$C_dH_eF_f \quad (3)$$

where d, e, and f are respectively an integer satisfying the relations: $2 \leq d \leq 3$, $0 \leq e \leq 5$, $1 \leq f \leq 6$; and e+f=4 for d=2, and e+f=6 for d=3.

(32) The process for producing a halogen compound as described in (31) above, wherein the hydrofluorocarbon is at least one selected from the group consisting of trifluoromethane, 1,1,1,2-tetrafluoroethane, pentafluoroethane, hexafluoropropane, and heptafluoropropane.

(33) The process for producing a halogen compound as described in (31) above, wherein the fluoroolefin is at least one selected from the group consisting of tetrafluoroethylene, trifluoroethylene, and hexafluoropropene.

(34) The process for producing a halogen compound as described in (30) above, wherein the concentration of the fluorine gas is controlled to be not higher than the explosion range thereof.

(35) A process for producing a perfluorocarbon by reacting a hydrofluorocarbon with fluorine gas in a gas phase, wherein the concentration of the hydrofluorocarbon is controlled by the method for measuring a hydrofluorocarbon concentration as described in (13) above.

(36) The process for producing a perfluorocarbon as described in (35) above, wherein the concentration of the hydrofluorocarbon is controlled to be not higher than 8 mole %.

(37) The process for producing a perfluorocarbon as described in (35) or (36) above, wherein the hydrofluorocarbon is represented by General Formula (1):

$$C_xH_yF_z \quad (1)$$

where x, y, and z are respectively an integer satisfying the relations: $1 \leq x \leq 3$, $1 \leq y \leq 4$, $1 \leq z \leq 7$, and 2x+2=y+z.

(38) The process for producing a perfluorocarbon as described in (37) above, wherein the hydrofluorocarbon is at least one selected from the group consisting of trifluoromethane, 1,1,1,2-tetrafluoroethane, and pentafluoroethane.

BRIEF DESCRIPTION OF THE DRAWINGS

FIG. 1 is a schematic drawing of an embodiment of the halogen concentration measurement apparatus of the present invention.
1 Gas flow rate controller
3 Liquid feed pump
4 Reaction section
5 Gas-liquid separation section
7 Halogen concentration measurement section
8 Laser beam controller
9 Laser beam emitter
10 Aqueous solution flow path
11 Laser beam receiver
12 Laser beam transmittance detector
13 Data processor
FIG. 2 shows schematically a flow diagram of perfluorocarbon production of an embodiment of the present invention.
21 First reaction zone
22 Second reaction zone
23 Distillation-purification section
24 Fluorine gas fed to first reaction zone
25 Hydrofluorocarbon fed to first reaction zone
26 Gas mixture fed to first reaction zone
27 Gas mixture discharged from first reaction zone
28 Fluorine gas fed to second reaction zone
29 Hydrofluorocarbon fed to second reaction zone
30 Gas mixture fed to second reaction zone
31 Gas mixture discharged from second reaction zone
32 Diluting gas
33 Gas introduced into distillation-purification step
34 Fluorine gas measurement apparatus

FIG. 5 shows schematically a flow diagram of perfluorocarbon production of another embodiment of the present invention.
11' First reaction zone
12' Second reaction zone
13' Distillation-purification step
14' Fluorine gas fed to first reaction zone
15' Hydrofluorocarbon fed to first reaction zone
16' Gas component fed to first reaction zone
17' Gas component discharged from first reaction zone
18' Fluorine gas fed to second reaction zone
19' Hydrofluorocarbon fed to second reaction zone
20' Gas component fed to second reaction zone
21' Gas component discharged from second reaction zone
22' Diluting gas
23' Gas introduced into distillation-purification step
24' Infrared measurement apparatus 1
25' Infrared measurement apparatus 2

DETAILED DESCRIPTION OF THE INVENTION

The present invention is described below in more detail.

In this specification, the word of "apparatus" has the same meaning with that of "equipment".

In conducting a halogenation reaction by use of a halogen gas, it is important to keep the concentration of the remaining halogen gas in a suitable range, as mentioned before. The present invention has advantages (1) to (3) below, and enables continuous measurement of a halogen gas concentration with high responsiveness in a halogen compound production plant.

(1) Stability of measurement of a halogen gas concentration of several-thousand ppm or less with little or no maintenance for a long term;
(2) Small space required for apparatus installation; and
(3) High response speed, enabling process control feedback.

The present invention will be explained in detail.

The measurement of the halogen concentration in the present invention is based on the known reaction in which contact of an oxidative agent like fluorine or chlorine with an aqueous solution containing a metal iodide causes reaction to liberate iodine. The metal iodide is preferably potassium iodide. The aqueous solution containing liberated iodine assumes a yellow color at a low iodine concentration, and the color turns reddish yellow with increase of the iodine concentration. Starch added to the aqueous metal iodide solution interacts with the liberated iodine to develop a blue color. The quantity of the liberated iodine can be determined by projecting, to the yellow or blue solution, visible blue to red light of a specified wavelength and measuring the light transmittance. Therefrom, the halogen concentration in the gas is derived.

In an aqueous potassium iodide solution, the iodine develops a color ranging from yellow to reddish yellow: the iodine can be quantitatively determined by projecting light of from blue to green selected in a wavelength region ranging from 460 nm to 520 nm, and measuring the light transmittance. On the other hand, with starch added to the aqueous potassium iodide solution, the solution develops blue color: the iodine can be quantitatively determined by projecting red light selected in a wavelength region ranging from 580 nm to 780 nm, and measuring the light transmittance.

The light source for the visible light includes tungsten lamps, xenon lamps, and quartz-iodine lamps. Light-emitting diodes, and laser diodes are also useful therefor. The light source is used in combination with a spectroscope to obtain the selected wavelength.

Next, the continuous method of measuring a halogen concentration of the present invention is explained below by reference to an example of analysis of fluorine in a gas employing a laser as the light source.

The measurement of the halogen concentration of the present invention comprises the steps (1) to (5) below:
(1) An aqueous potassium iodide solution containing or not containing starch is allowed to flow through a reaction section at a constant flow rate, and a fluorine-containing process gas is blown into the aqueous solution to liberate iodine continuously.
(2) The aqueous solution develops color of yellow to reddish yellow of iodine liberated by reaction of fluorine gas with potassium iodide, or blue color caused by interaction of the liberated iodine with added starch.
(3) An insoluble gas component is removed by gas-liquid separation, when the process gas contains an insoluble gas like nitrogen in a large amount, and the liquid layer only is introduced to the concentration measurement section.
(4) A selected laser beam is projected from outside of a transparent tube in the concentration measurement section, and the laser beam transmittance of the solution is measured with a laser beam receiver placed on the reversed side.
(5) The fluorine concentration in the measured gas is calculated by reference to the relation between the laser beam transmittance and the liberated iodine.

In the present invention, the solution for liberation of iodine may be an aqueous potassium iodide solution containing or not containing starch. However, the aqueous iodide solution containing starch is preferred. When the starch-containing solution is used, the iodine solution develops blue color, and visible light in a red region is projected thereto. Preferably the light is a laser beam of high directivity. The light source is preferably a semiconductor laser. The wavelength is selected in the range from 580 nm to 780 nm, preferably from 600 nm to 700 nm.

The iodine concentration to be measured is preferably not higher than $3 \times 10^{-3}$ mol/L. A higher iodine concentration will render the measurement results unstable. Therefore, the concentration and the amount of the potassium iodide and the starch in the aqueous solution introduced into the reaction section, and the amount of the gas introduced into the reaction section are selected so as not to exceed the above range. The responsiveness can be adjusted by the flow rate of the solution introduced into the reaction section, the higher flow rate shortening the response time.

The present invention relates to a process for producing a perfluorocarbon by direct fluorination of a hydrofluorocarbon with fluorine gas in a gas phase, wherein the concentration of at least one kind of hydrofluorocarbon in a gas mixture is measured by infrared spectrometry. The gas mixture may contain at least one kind of perfluorocarbon, hydrogen fluoride, and fluorine gas besides the hydrofluorocarbon. The perfluorocarbon and the hydrogen fluoride can be determined simultaneously by infrared spectroscopy in a similar manner as the hydrofluorocarbon.

The hydrofluorocarbon is at least one of the hydrofluorocarbons represented by General Formula (1):

$$C_xH_yF_z \quad (1)$$

where x, y, and z are respectively an integer satisfying the relations: $1 \leq x \leq 3$, $1 \leq y \leq 4$, $1 \leq z \leq 7$, and $2x+2=y+z$. The hydrofluorocarbon is preferably trifluoromethane, 1,1,1,2-tetrafluoroethane, and/or pentafluoroethane.

The perfluorocarbon is at least one compound selected from the group consisting of tetrafluoromethane, hexafluoroethane, and octafluoropropane; preferably tetrafluoromethane and/or hexafluoroethane.

In the method for measuring the hydrofluorocarbon of the present invention, the concentration of the hydrofluorocarbon may be at an arbitrary level in relation with HF and the perfluorocarbon. However, the hydrofluorocarbon as the reaction base material is liable to burn or explode upon contact with fluorine, since the reaction of the organic compound with $F_2$ generates a great quantity of heat as mentioned above. For example, the lower limit of the explosion range of a mixture of a hydrofluorocarbon and $F_2$ is about 6% for pentafluoroethane, about 4% for 1,1,1,2-tetrafluoroethane. Therefore, the mixture composition is limited for safety of the reaction process.

To introduce the gas mixture into the measurement cell, the reaction gas is continuously passed through the cell, or is continuously sampled through a switching valve from the reactor. The measurement cell may be provided in two series or more for shortening the measurement time. The switching valve may be driven for switching in any method, preferably driven automatically by an electric driving force or a pneumatic driving force. The switching valve may be controlled for switch timing by a controller having switching program installed therein. The switching valve, the gas introduction tube for introducing the gas to the measurement cell, and the measurement cell are preferably heated to prevent condensation of the gas mixture. The temperature thereof is preferably 20° C. or higher, more preferably 3° C. or higher. The inside of the tubing and measurement cell not in use for the measurement may be purged with a clean dry gas, or preliminarily replaced with the gas mixture.

The measurement wavenumber in the infrared spectrometry depends on the component to be measured in the gas mixture, and is suitably selected. For hydrofluorocarbons, the wavenumber is selected in the range of 2900 cm$^{-1}$~3100 cm$^{-1}$ which is considered to correspond to the C—H stretching vibration. For example, trifluoromethane concentration can be measured in the wavenumber range of 3033 cm$^{-1}$~3037 cm$^{-1}$; 1,1,1,2-tetrafluoroethane in 2981 cm$^{-1}$~2986 cm$^{-1}$ or 3011 cm$^{-1}$~3014 cm$^{-1}$; and pentafluoroethane in 2996 cm$^{-1}$~3006 cm$^{-1}$, but the wavenumber is not limited thereto.

For perfluorocarbons, the wavenumber is selected in the range of 1000 cm$^{-1}$~2700 cm$^{-1}$ which is considered to correspond to the C—F stretching vibration or deformation vibration. For example, tetrafluoromethane concentration can be measured in the wavenumber range of 1500 cm$^{-1}$~1535 cm$^{-1}$, 1535 cm$^{-1}$~1540 cm$^{-1}$, 1540 cm$^{-1}$~1585 cm$^{-1}$, 2120 cm$^{-1}$~2150 cm$^{-1}$, or 2150 cm$^{-1}$~2210 cm$^{-1}$, and so forth; and hexafluoroethane in 1420 cm$^{-1}$~1490 cm$^{-1}$, 1570 cm$^{-1}$~1670 cm$^{-1}$ 2030 cm$^{-1}$~2080 cm$^{-1}$~2300 cm$^{-1}$~2380 cm$^{-1}$, or 2630 cm$^{-1}$ 18 2690 cm$^{-1}$, and so forth, but the wavenumber is not limited thereto.

Similarly, the hydrogen fluoride concentration in the gas mixture can be measured at a wavenumber selected in the range of 3600 cm$^{-1}$~4300 cm$^{-1}$: for example, at the wavenumber of 4160 cm$^{-1}$~4190 cm$^{-1}$, 4190 cm$^{-1}$~4220 cm$^{-1}$, 4220 cm$^{-1}$~4240 cm$^{-1}$, 4245 cm$^{-1}$~4270 cm$^{-1}$, 4270 cm$^{-1}$~4290 cm$^{-1}$, and so forth, but is not limited thereto.

Figure 1:
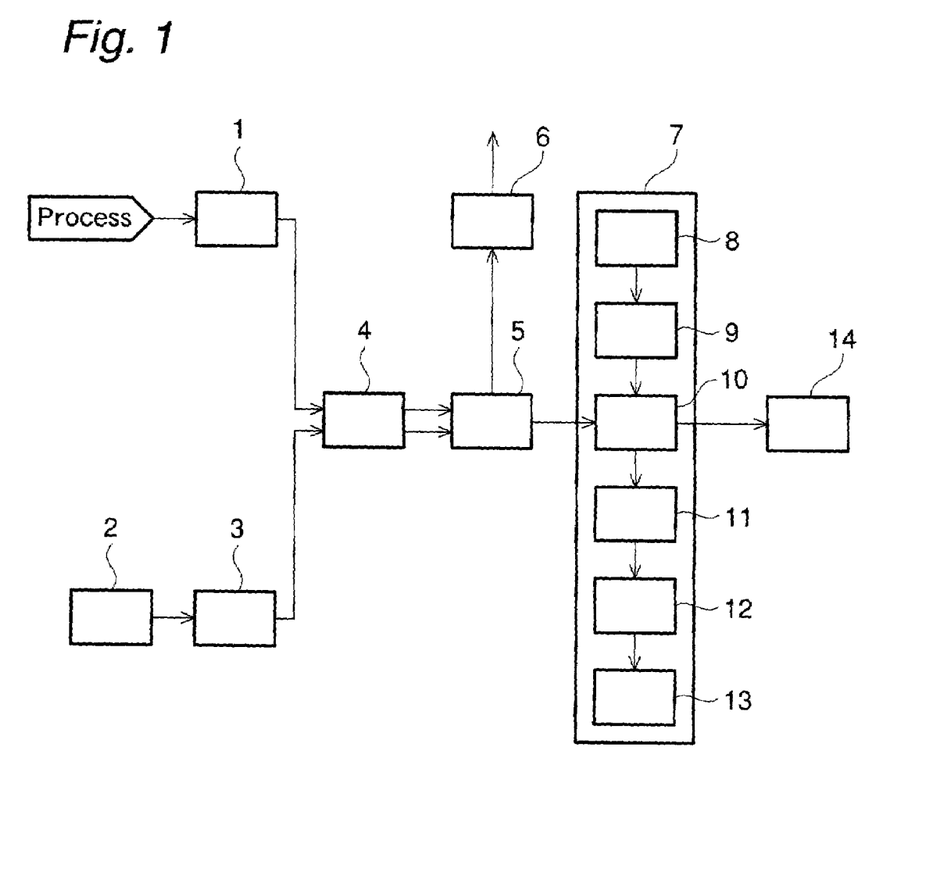

The measurement apparatus for continuous measurement of the halogen concentration is explained below FIG. 1 is a schematic drawing of a measurement apparatus of an embodiment of the present invention. In this embodiment, the halogen-containing gas is introduced into a solution containing potassium iodide as the metal iodide and starch added thereto, and a semiconductor laser of wavelength 670 nm is used as the visible light source.

In FIG. 1, through a reaction section 4, a solution containing potassium iodide and starch is allowed to flow at a constant flow rate. A gas flow rate controller 1 is connected to an introduction tube not shown in the drawing, and introduces a part of the process gas containing halogen gas sampled through the introduction tube at a controlled flow rate into the reaction section 4. A gas-liquid separation section 5 separates a water-insoluble diluent gas like nitrogen to prevent fluctuation of the measurement value. A halogen concentration measurement section 7 has a laser beam controller 8, a laser beam emitter 9, an aqueous solution flow path 10, a laser beam receiver 11, a laser beam transmittance detector 12, and a data processor 13. The data processor 13 may be connected to a display for showing the halogen concentration, or a printer for recording the concentration, or may be designed to produce a warning sound when the halogen concentration exceed a set level.

The construction materials for the respective apparatuses are suitably selected from corrosion-resistant materials to meet the corrodibility of the parts, since the corrodibility is greatly different between the gas-contacting part and the liquid-contacting part. The surfaces of the gas-introduction tube, the gas flow rate controller, and the reaction section which are brought into contact with the halogen-containing gas may be formed from a metal, the metal surface being preferably passivated, for example by fluorine gas. The liquid-contacting portion where the hydrogen halide solution of a high concentration allowed to pass is preferably made of a fluororesin, especially in the case of fluorine owing to the high corrosivity of the hydrogen fluoride solution. The measurement portion which should be transparent to the visible light is preferably made from a tetrafluoroethylene-perfluoroalkyl vinyl ether copolymer (PFA).

The measurement apparatus for measuring a hydrofluorocarbon concentration of the present invention is explained below.

Figure 4:
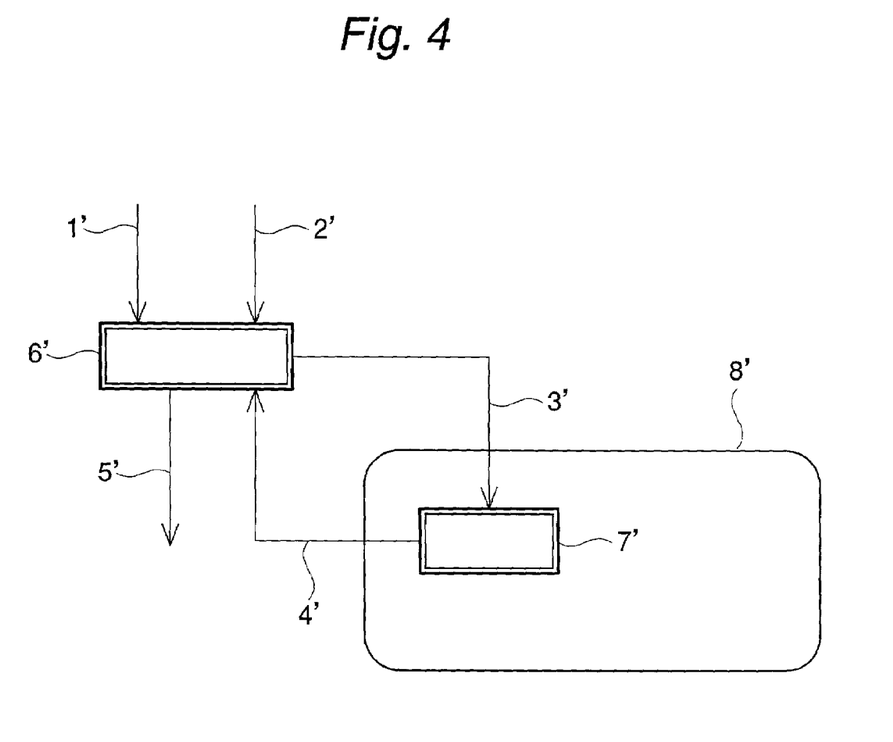
FIG. 4 shows schematically a measurement apparatus for measuring a hydrofluorocarbon concentration of an embodiment of the present invention.
1' Reaction gas introduction tube
2' Purge gas introduction tube
3' Gas introduction tube
4' Gas discharge tube
5' Pollution prevention line
6' Automatic control/switching valve for gas introduction
7' Measurement cell
8' Infrared measurement apparatus

FIG. 4 is a schematic drawing showing the apparatus of an embodiment of the present invention. A measurement cell 7' has a heating means. An automatic switching valve 6' is connected with an introduction tube 1' for sampling a part of the reaction gas from the perfluorocarbon production line and with a purge gas introduction tube 2', and introduces the reaction gas or the purge gas into the measurement cell 7'. The numeral 8' indicates an infrared measurement apparatus. An introduction tube 3' introduces the reaction gas and the purge gas into the measurement cell 7'. A discharge tube 4' discharges the gas from the measurement cell 7'.

The reaction gas or the purge gas is introduced by changing the setting of the automatic switching valve 6' into the measurement cell 7', and the discharged gas is introduced into the discharge tube 4' and pollution-prevention line 5' and is discharged out of the system. In measuring the concentration of the reaction gas component, the reaction gas is allowed to flow, until the concentration of the reaction gas reaches a constant value. Then the inlet and the outlet of the cell is closed to seal the gas therein. After the measurement, preferably the purge gas is allowed to pass sufficiently to remove a condensed gas component on the measurement cell wall. Instead, before the next measurement, the reaction gas may be allowed to pass through until the concentration of the reaction gas reaches a constant value, and then the gas is sealed for the measurement. In any way, the measurement cell is kept preferably at a temperature not lower than 20° C.

In the measurement apparatus, the automatic switching valve 6', gas tubes 1'~5', and the measurement cell are preferably resistant against the corrosion by HF and $F_2$. The metal material therefor includes preferably stainless steel, monel metal, and inconel alloy. The optical material (window material of the measurement cell) is preferably a metal halide which transmits infrared ray. The metal halides includes lithium fluoride, sodium fluoride, calcium fluoride, magnesium fluoride, strontium fluoride, and barium fluoride. Of these, calcium fluoride is preferred.

The infrared spectrophotometer is preferably of a Fourier transform type. The data processor has a calibration curve installed therein, and from the result of measurement by the analyzer, determines quantitatively the hydrofluorocarbon, the perfluorocarbon, and/or hydrogen fluoride. The date processor may be have a function of transforming the determination results to electric signals to display the results on a separate display device.

The process for producing a halogen compound by adjusting the halogen concentration with the method for measuring a halogen concentration of the present invention is explained below.

Figure 2:
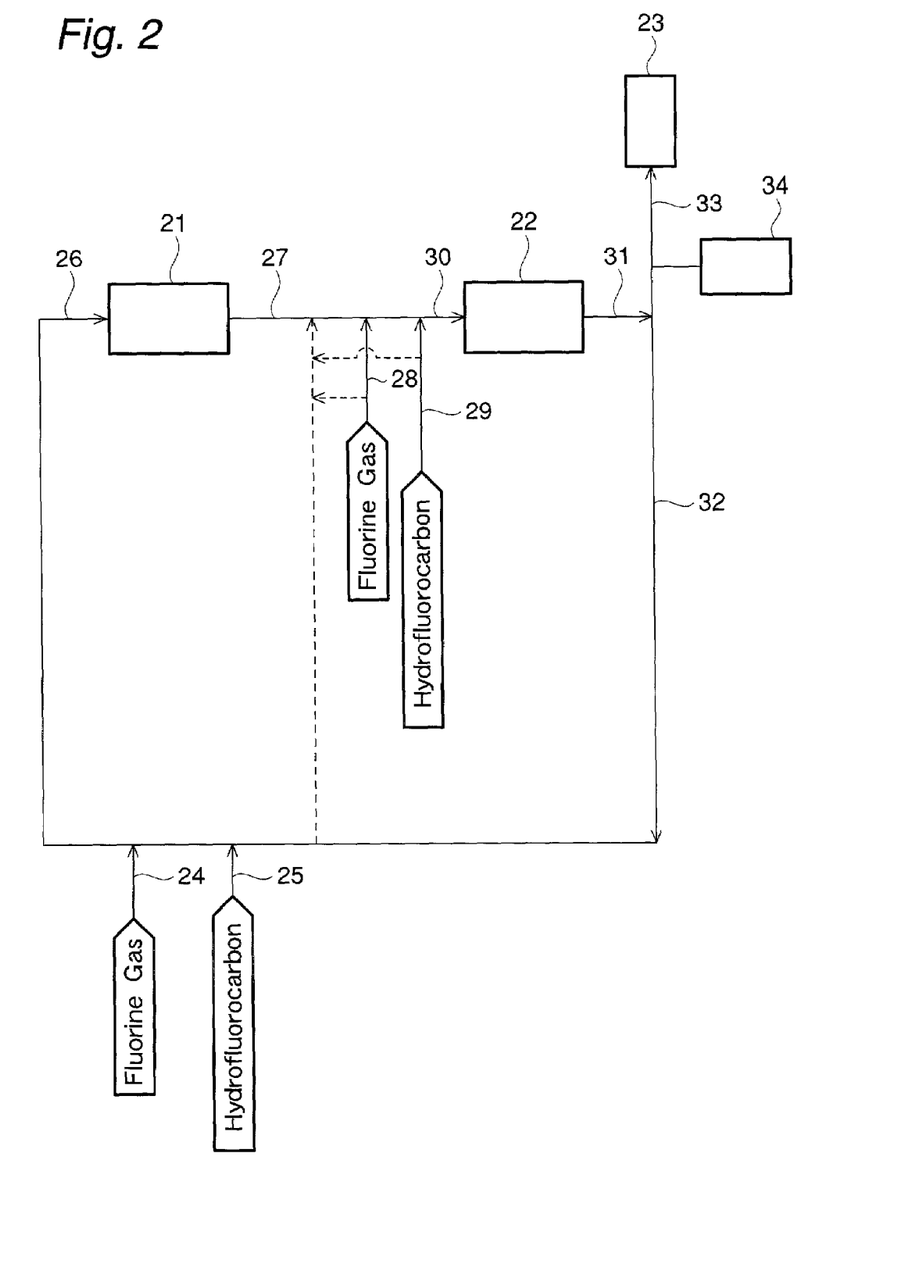

FIG. 2 shows schematically a process flow diagram of a fluorine compound production of an embodiment of the present invention. In this embodiment, a production plant having two reaction zones produces one or two different compounds. In FIG. 2, in a first reaction zone 21, fluorine gas fed from a tube 24 and hydrofluorocarbon fed from a pipe 25 are allowed to react. In a second reaction zone 22, the reaction gas having been formed in the first reaction zone is used as the diluent gas, and fluorine gas fed from a tube 28 and hydrofluorocarbon fed from a pipe 29 are allowed to react. A part 33 of a discharged gas 31 from the second reaction zone is introduced to a distillation-purification section, and the other part 32 of the gas 31 is recycled as a diluent gas to the first reaction zone and/or the second reaction zone. A measurement apparatus 34, which is the one shown in FIG. 1 is capable of measuring and controlling the fluorine concentration in the entire production plant. In the two-step reaction shown in FIG. 2, the fluorine concentration can be more precisely controlled by installing the measurement apparatus for each of the reaction steps.

The aforementioned hydrofluorocarbon is at least one represented by General Formula (2):

$$C_aH_bF_c \quad (2)$$

where a, b, and c are respectively an integer satisfying the relations: $1 \leq a \leq 3$, $1 \leq b \leq 4$, $1 \leq c \leq 7$; and b+c=4 for a=1, b+c=6 for a=2, and b+c=8 for a=3; the hydrofluorocarbon including preferably trifluoromethane, 1,1,1,2-tetrafluoroethane, pentafluoroethane, hexafluoropropane, and heptafluoropropane.

A fluoroolefin represented by General Formula (3) can be used in place of the above hydrofluorocarbon:

$$C_dH_eF_f \quad (3)$$

where d, e, and f are respectively an integer satisfying the relations: $2 \leq d \leq 3$, $0 \leq e \leq 5$, $1 \leq f \leq 6$; and e+f=4 for d=2, and e+f=6 for d=3; the fluoroolefin including preferably tetrafluoroethylene, trifluoroethylene, and hexafluoropropene.

In the reaction of the hydrofluorcarbon or the fluoroolefin with fluorine gas, the composition of the gas mixture should be controlled not to come into the explosion range, and to be kept in a safe composition ratio below the lower explosion limit depending on the kind of the compound employed.

The process for producing a perfluorocarbon by adjusting a hydrofluorcarbon concentration by the method for measuring a hydrofluorocarbon concentration of the present invention is explained below.

Figure 5:
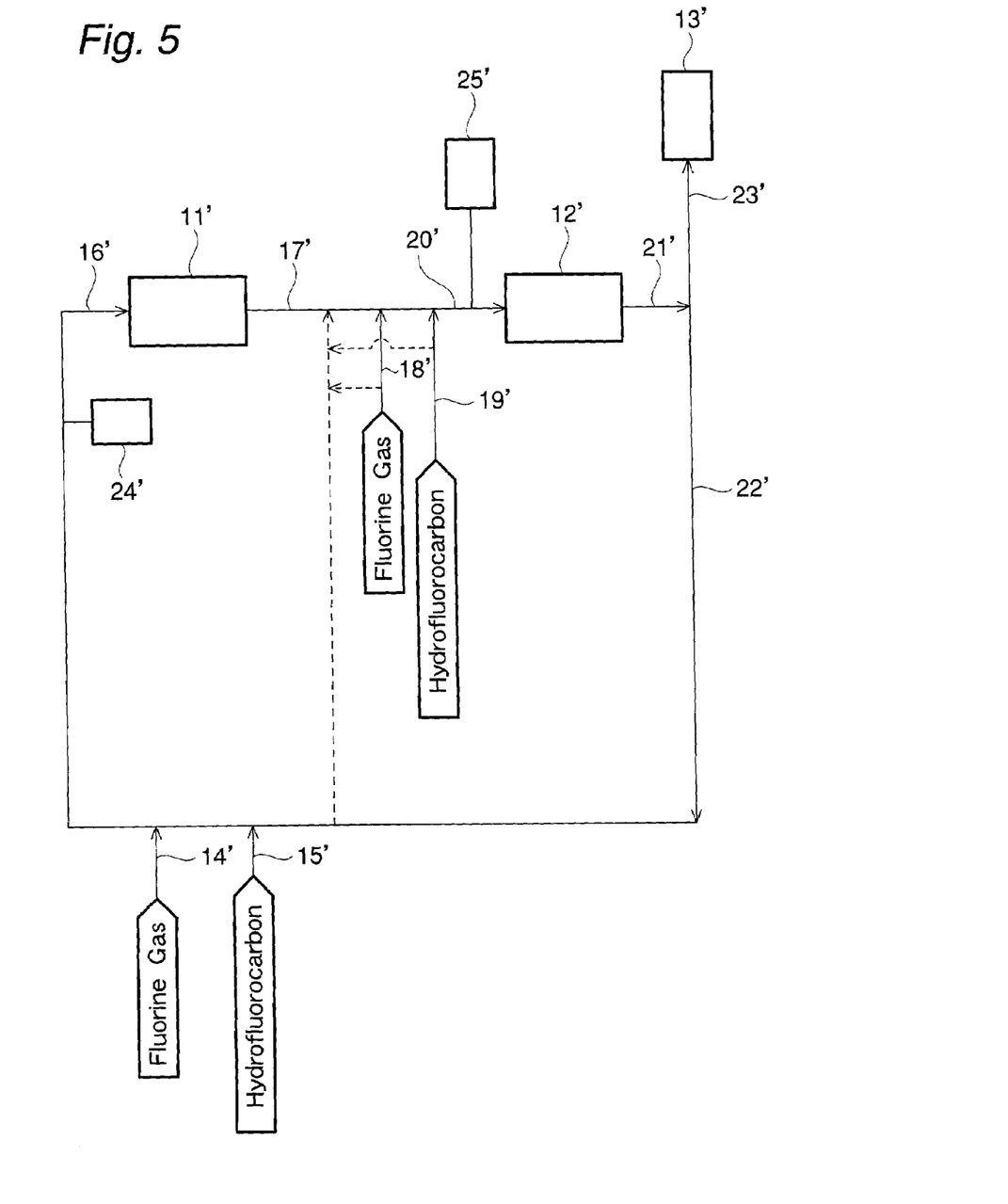

FIG. 5 shows schematically a process flow diagram of a fluorine compound production of an embodiment of the present invention. In this embodiment, a production plant having two reaction zones produces one or two different compounds. In FIG. 5, in a first reaction zone 11', fluorine gas fed from a tube 14' and hydrofluorocarbon fed from a pipe 15' are allowed to react. In a second reaction zone 12', the reaction gas having been formed in the first reaction zone is used as the diluent gas, and fluorine gas fed from a tube 18' and hydrofluorocarbon fed from a pipe 19' are allowed to react. A part 23' of a discharged gas 21' from the second reaction zone is introduced to a distillation-purification section, and the other part 22' of the discharged gas 21' is recycled as a diluent gas to the first reaction zone and/or the second reaction zone. Infrared measurement apparatuses 24', 25', which are respectively the one shown in FIG. 4, are set respectively before the first reaction zone or the second reaction zone to measure the hydrofluorocarbon concentration. The infrared measurement apparatus may be set after the first reaction zone 11' and the second reaction zone 12', whereby the remaining hydrofluorocarbon can be measured.

The aforementioned hydrofluorocarbon is at least one of the hydrofluorocarbons represented by General Formula (1):

$$C_xH_yF_z \quad (1)$$

where x, y, and z are respectively an integer satisfying the relations: $1 \leq x \leq 3$, $1 \leq y \leq 4$, $1 \leq z \leq 7$, and 2x+2=y+z; the hydrofluorocarbon including preferably trifluoromethane, 1,1,1,2-tetrafluoroethane, and pentafuoroethane.

In the reaction of the hydrofluorcarbon with fluorine gas, the composition of the gas mixture should be controlled not to come into the explosion range, and to be kept in a safe composition ratio below the lower explosion limit depending on the kind of the compound employed.

EFFECTS OF THE INVENTION

The present invention relates to indirect measurement of a halogen concentration by bringing the halogen into contact with a metal iodide compound solution to liberate iodine and measuring the liberated iodine by transmittance of visible light. This has made possible continuous measurement of a halogen gas concentration in a reaction gas, which has been difficult until now. By the measurement method of the present invention, the halogen concentration in a halogen compound production plant can be adjusted simply to be a prescribed level economically. The method of the present invention is applicable also to continuous measurement of not only the halogen-containing gas but also of a halogen-oxygen acid salt or the like in an aqueous solution.

Further, the method of measuring a hydrofluorocarbon concentration of the present invention enables safe and quick determination of a hydrofluorocarbon, a perfluorocarbon, and/or hydrogen fluoride in direct fluorination of a hydrofluorocarbon as the reaction base material by $F_2$.

EXAMPLES

The present invention is explained below in more detail by reference to examples without limiting the invention thereto.

(Preparation of Potassium Iodide-Starch Solution)
(1) Potassium iodide solution: 10 g of potassium iodide was dissolved in 1 L of pure water.
(2) Starch solution: 1 g of starch was put into 200 mL of pure water. The mixture was heated to 50° C., and stirred. After left standing for 30 minutes, 100 mL of the supernatant liquid was collected as the starch solution.
(3) Potassium iodide-starch solution: 1 mL of the above starch solution was added to 99 mL of the above potassium iodide solution to obtain the potassium iodide-starch solution.

Figure 3:
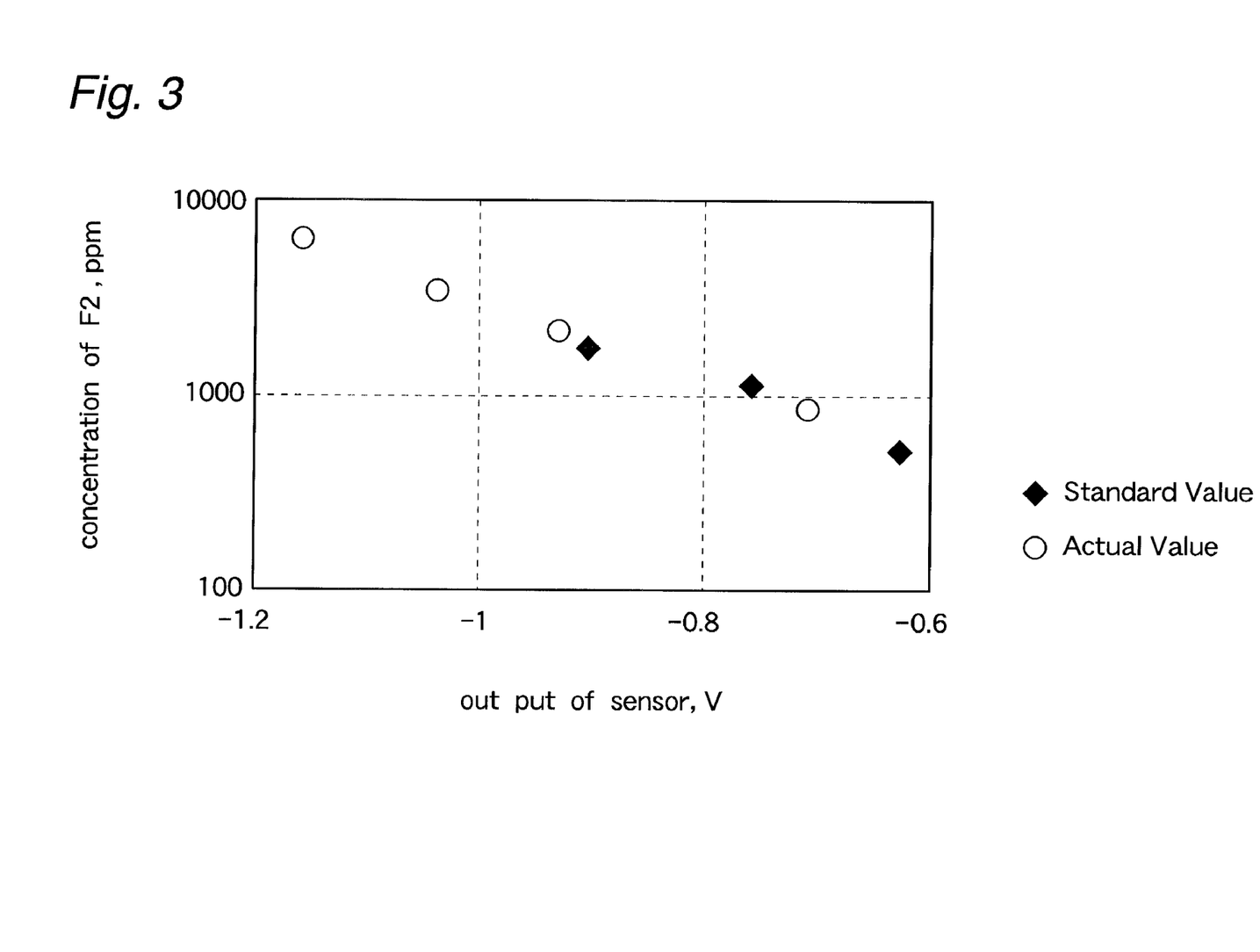
FIG. 3 shows relation between the fluorine concentration and output of photosensor.

(Measurement of Iodine Concentration)
The relation between the iodine concentration and the output level of the red-color laser beam sensor was derived by use of the apparatus shown in FIG. 1, Table 1 shows the result. Corresponding to the practical measurement conditions, the potassium iodide-starch solution and the process gas were allowed to flow through the reaction section at rates of 2 mL/min and 20 mL/min respectively. In this state, the three iodine concentration levels shown below correspond to specified fluorine concentrations. The corresponding fluorine concentrations are shown in Table 1, and shown also in FIG. 3 as the standard values.

(1) A fluorine-containing gas was blown into the potassium iodide-starch solution to prepare three solutions having different colors. The iodine concentration of the solutions were determined by titration with sodium thiosulfate.
(2) The above three solutions were subjected to measurement of optical sensor output by projecting a red laser beam of 670 nm in the measurement section shown in FIG. 1.

TABLE 1

| Iodine concentration (mol/L) | Optical sensor output (V) | Corresponding fluorine concentration (ppm) |
| --- | --- | --- |
| $7.6 \times 10^{-4}$ | −0.903 | 1700 |
| $4.6 \times 10^{-4}$ | −0.760 | 1100 |
| $2.3 \times 10^{-4}$ | −0.630 | 500 |

Example 1

Trifluoromethane (HFC-23) was directly fluorinated in the presence of a diluent gas in a continuous process to produce tetrafluoromethane (FC-14). The fluorine gas concentration in the process gas under four different conditions was measured with the apparatus shown in FIG. 1. In the measurement, the potassium iodide-starch solution and the process gas were allowed to flow through the reaction section at flow rates of 2 mL/min and 20 mL/min respectively in the same manner as mentioned above. The fluorine gas concentration was derived from the output of the optical sensor, and was also confirmed simultaneously by titration with sodium thiosulfate. The concentration measured by the sodium thiosulfate titration, and the output levels of the optical sensor are shown Table 2 and FIG. 3. The output levels of the optical sensor are on the same line as the standard values shown in FIG. 3, which shows the high reliability of the results of the measurement of remaining fluorine gas concentration.

TABLE 2

| Fluorine concentration (ppm) | Optical sensor output (V) |
| --- | --- |
| 800 | −0.710 |
| 2100 | −0.930 |
| 3500 | −1.040 |
| 6400 | −1.160 |

Example 2

The process in FIG. 2 for producing perfluorocarbon is explained. Trifluoromethane as the hydrofluorocarbon (25 in FIG. 2) and fluorine gas (24 in FIG. 2) were mixed with a diluent gas (32 in FIG. 2), and the gas mixture (26 in FIG. 2) was introduced into a first reaction zone (21 in FIG. 2). In the first reaction zone, the reaction was allowed to proceed under the conditions of the reaction pressure of 1.5 MPa, the reaction temperature of 400° C., the molar ratio of $F_2$/trifluoromethane of 1.51, and the trifluoromethane concentration at the inlet of 2.1 mole % to obtain an outlet gas (27 in FIG. 2) of the first reaction zone.

To this outlet gas, 1,1,1,2-tetrafluoroethane as a new hydrofluorocarbon (29 in FIG. 2), and fluorine gas (28 in FIG. 2) were added. The gas mixture (30 in FIG. 2) was introduced to a second reaction zone (22 in FIG. 2). In the second reaction zone, the reaction was allowed to proceed under the conditions of the reaction pressure of 1.5 MPa, the reaction temperature of 370° C., the molar ratio of $F_2$/1,1,1,2-tetrafluoroethane of 2.06, and the 1,1,1,2-tetrafluoroethane concentration at the inlet of 1.35 mole % to obtain an outlet gas (31 in FIG. 2) of the second reaction zone. This outlet gas was separated into a diluent gas (32 in FIG. 2) and a gas (33 in FIG. 2) to be distilled and purified. The results are shown in Table 3. The reference numerals are the same as those in FIG. 2. In Table 3, the fluorine gas concentrations of the component 33 were measured with the apparatus shown in FIG. 1 The concentrations were in good agreement with the results of the sodium thiosulfate titration, which shows the practicableness of the continuous measurement of a low concentration of fluorine gas.

TABLE 3

| Component | 24 | 25 | 26 | 27 | 28 | 29 | 30 | 31 | 32 | 33 |
| --- | --- | --- | --- | --- | --- | --- | --- | --- | --- | --- |
| $F_2$ | 1.003 | | 1.012 | 0.367 | 0.585 | | 0.952 | 0.010 | 0.009 | 0.001 |
| HFC-134a | | | 0.004 | | | 0.462 | 0.462 | 0.004 | 0.004 | |
| HFC-23 | | 0.665 | 0.668 | 0.047 | | | 0.047 | 0.003 | 0.003 | |
| HF | | | 17.288 | 17.933 | | | 17.933 | 18.873 | 17.288 | 1.585 |
| HFC-125 | | | 0.030 | 0.015 | | | 0.015 | 0.033 | 0.030 | 0.003 |
| FC-116 | | | 4.983 | 5.002 | | | 5.002 | 5.440 | 4.983 | 0.457 |
| FC-14 | | | 7.295 | 7.916 | | | 7.916 | 7.964 | 7.295 | 0.669 |
| Others | 0.010 | 0.001 | 0.031 | 0.031 | 0.007 | | 0.038 | 0.038 | 0.020 | 0.018 |
| Total | 1.013 | 0.666 | 31.489 | 31.489 | 0.592 | 0.462 | 32.365 | 32.365 | 29.632 | 2.733 |

Unit of the components: Kmol/hr
HFC-134a: 1,1,1,2-Tetrafluoroethane
HFC-23: Trifluoromethane
HFC-125: Pentafluoroethane

Example 3

A reactor employed had an inner diameter of 20.6 mm. a length of 500 mm, being made of inconel 600, being of an electric heater type, and having been passivated by fluorine gas at 600° C. The reactor was heated to 280° C. with passage of a diluent gas (composed of 41.8 vol % of tetrafluoromethane as a perfluorocarbon, and 58.2 vol % hydrogen fluoride) at a flow rate of 50 NL/h. To one portion of the separated diluent gas flow, 1,1,1,2-tetrafluoroethane was introduced as a hydrofluorocarbon at a flow rate of 1.0 NL/h. Similarly, to the other portion of the separated diluent gas flow, fluorine gas was introduced at a flow rate of 2.0 NL/h to cause direct fluorination. A part of the reactor inlet gas was introduced into a heated measurement cell (window material: calcium fluoride) by an automatic switching valve made of SUS316 driven pneumatically, and was subjected to infrared spectrum measurement by an infrared spectrophotometer.

Table 4 shows the infrared absorption spectrum wave-number for measuring the concentrations of the compounds.

TABLE 4

| Compound | Wavenumber |
| --- | --- |
| Trifluoromethane | 3033 $cm^{-1}$~3037 $cm^{-1}$ |
| 1,1,1,2-Tetrafluoroethane | 2981 $cm^{-1}$~2986 $cm^{-1}$ or 3011 $cm^{-1}$~3014 $cm^{-1}$ |
| Pentafluoroethane | 2996 $cm^{-1}$~3006 $cm^{-1}$ |
| Tetrafluoromethane | 1542 $cm^{-1}$~1585 $cm^{-1}$ |
| Hexafluoroethane | 2630 $cm^{-1}$~2690 $cm^{-1}$ |
| Hydrogen fluoride | 4228 $cm^{-1}$~4235 $cm^{-1}$ |

The components contained in the reactor inlet were determined. Table 5 shows the results.

TABLE 5

| Compound | Measurement result |
| --- | --- |
| Trifluoromethane | <0.1 vol % |
| 1,1,1,2-tetrafluoroethane | 2.0 vol % |
| Pentafluoroethane | <0.1 vol % |
| Hexafluoroethane | <0.1 vol % |
| Tetrafluoromethane | 39.2 vol % |
| Hydrogen fluoride | 54.8 vol % |

Example 4

The gas mixture shown in Example 3 was tested for direct fluorination at the reactor temperature of 280° C. The gas at the reactor outlet was analyzed in the same manner as in Example 3. Table 6 shows the results.

TABLE 6

| Compound | Measurement result |
| --- | --- |
| Trifluoromethane | <0.1 vol % |
| 1,1,1,2-tetrafluoroethane | <0.1 vol % |
| Pentafluoroethane | 0.3 vol % |
| Hexafluoroethane | 1.7 vol % |
| Tetrafluoromethane | 39.3 vol % |
| Hydrogen fluoride | 58.7 vol % |

Comparative Example 1

The gas mixture having the composition as shown in Example 3 was analyzed in a conventional manner. The reactor inlet gas was washed with a potassium iodide solution. The gas was allowed to pass the washing bottle until the gas leaving the gas washing bottle amounted to 5 L in total. After the gas washing bottle and the gas meter for measuring the amount of the gas was completely purged with the washed gas, the washed gas was collected into a fluororesin bag. A portion of the washing solution was taken, and the contents of the hydrogen fluoride and $F_2$ in the gas mixture were determined by neutralization titration and iodometric titration. Separately, a portion of the washed gas was analyzed by gas chromatography to determine the gas composition.

Table 7 shows the concentrations of the acidic gas components and the fluorine compounds. The results are nearly the same as the results of Example 3. However, a long time of 1 hour and 30 minutes was required from the gas sampling to completion of the entire analysis.

TABLE 7

| Compound | Measurement result |
| --- | --- |
| Trifluoromethane | <0.1 vol % |
| 1,1,1,2-tetrafluoroethane | 2.0 vol % |
| Pentafluoroethane | <0.1 vol % |
| Hexafluoroethane | <0.1 vol % |
| Tetrafluoromethane | 39.3 vol % |
| Hydrogen fluoride | 54.7 vol % |
| Fluorine gas | 4.0 vol % |

Example 5

The reaction was conducted under the same conditions as in Example 3. During the reaction, the reactor outlet gas was introduced to a measurement cell through a sampling system having an automatic switching valve. The gas components were determined at 15-minute intervals. Table 8 shows the results of measurement of HFC-125 and HFC-134a of which the concentration control is especially important for prevention of combustion or explosion. Both of the two components could be measured continuously and stably.

TABLE 8

| Lapse of time (min) | HFC-125 (vol %) | HFC-134a (vol %) |
| --- | --- | --- |
| 15 | <0.1 | <0.1 |
| 30 | 0.1 | <0.1 |
| 45 | 0.2 | <0.1 |
| 60 | <0.1 | <0.1 |
| 75 | <0.1 | <0.1 |
| 90 | 0.3 | <0.1 |
| 105 | 0.2 | <0.1 |
| 120 | 0.1 | <0.1 |
| 135 | <0.1 | <0.1 |
| 150 | <0.1 | <0.1 |

What is claimed is:

1. A method for measuring a halogen concentration comprising introducing a gas containing a halogen gas into a metal iodide-containing solution to liberate iodine, determining quantitatively the liberated iodine by measuring a visible light transmittance of the solution at wavelength ranging from 460 nm to 520 nm, and calculating the halogen concentration in the gas from the quantity of iodine liberated.

2. A method for measuring a halogen concentration comprising introducing a gas containing a halogen gas into metal iodide-containing solution which further contains starch to liberate iodine, determining quantitatively the liberated iodine by measuring a visible light transmittance of the solution at a specific wavelength, and calculating the halogen concentration in the gas from the quantity of iodine liberated.

3. The method for measuring a halogen concentration according to claim 2, wherein the specific wavelength ranges from 580 nm to 780 nm.

4. The method for measuring a halogen concentration according to claim 1 or 3, wherein the visible light is a laser beam.

5. The method for measuring a halogen concentration according to claim 1 or 2, wherein the halogen gas is chlorine gas or fluorine gas.

6. A method for continuously measuring a halogen concentration, comprising introducing continuously a gas containing a halogen gas into a continuously flowing metal iodide-containing solution to liberate iodine, determining quantitatively the liberated iodine by measuring a visible light transmittance of the solution at a wavelength ranging from 460 nm to 520 nm and calculating the halogen concentration in the gas from the quantity of iodine liberated.

7. A method for continuously measuring a halogen concentration comprising introducing continuously a gas containing a halogen gas into a continuously flowing metal iodide-containing solution which further contains starch to liberate iodine, determining quantitatively the liberated iodine by measuring a visible light transmittance of the solution concentration in the gas from the quantity of iodine liberated.

8. The method for continuously measuring a halogen concentration according to claim 7, wherein the specific wavelength ranges from 580 nm to 780 nm.

9. The method for continuously measuring a halogen concentration according to claim 6 or 8, wherein the visible light is a laser beam.

10. The method for continuously measuring a halogen concentration according to claim 6 or 7, wherein the halogen gas is chlorine gas or fluorine gas.

* * * * *